United States Patent [19]

Yoshida et al.

[11] Patent Number: 4,645,647
[45] Date of Patent: Feb. 24, 1987

[54] METHOD AND APPARATUS FOR CONTINUOUS FLOW ANALYSIS OF LIQUID SAMPLE

[75] Inventors: Kasumi Yoshida, Mito; Hideo Uchiki; Tadafumi Kuroishi, both of Katsuta, all of Japan

[73] Assignee: Hitachi, Ltd., Tokyo, Japan

[21] Appl. No.: 715,261

[22] Filed: Mar. 25, 1985

Related U.S. Application Data

[62] Division of Ser. No. 442,671, Nov. 18, 1982, Pat. No. 4,520,108.

[30] Foreign Application Priority Data

Nov. 20, 1981 [JP] Japan ................................ 56-185326

[51] Int. Cl.⁴ ...................... G01N 21/08; G01N 35/08
[52] U.S. Cl. .................................... 422/81; 422/103; 436/52; 436/164
[58] Field of Search ............ 73/864.81, 864.83, 864.84; 422/70, 81, 82, 78, 80, 103; 436/52, 53, 161, 164

[56] References Cited

U.S. PATENT DOCUMENTS

| | | | |
|---|---|---|---|
| 3,649,203 | 3/1972 | Schneider | 422/81 |
| 3,827,303 | 8/1974 | Shiina | 73/864.84 |
| 4,013,413 | 3/1977 | Stewart et al. | 436/52 |
| 4,022,575 | 5/1977 | Hansen et al. | 436/52 |
| 4,030,369 | 6/1977 | Etheridge | 73/864.83 |
| 4,274,967 | 6/1981 | Snyder | 422/70 |
| 4,312,635 | 1/1982 | Carlisle | 422/81 |
| 4,315,754 | 2/1982 | Ruzicka et al. | 436/52 |
| 4,504,443 | 3/1985 | Hansen et al. | 436/52 |

*Primary Examiner*—Michael S. Marcus
*Attorney, Agent, or Firm*—Antonelli, Terry & Wands

[57] ABSTRACT

A continuous flow analyzer of the type which introduces continuously a carrier liquid into a single tubular conduit to form a stable main carrier stream and injects predetermined volumes of reagent liquid and sample liquid in series into the main carrier stream. The analyzer reduces the consumption of the reagent and can form a stable continuous flow.

8 Claims, 7 Drawing Figures

METHOD AND APPARATUS FOR CONTINUOUS FLOW ANALYSIS OF LIQUID SAMPLE

This is a division of application Ser. No. 442,671, filed Nov. 18, 1982, now U.S. Pat. No. 4,520,108.

BACKGROUND OF THE INVENTION

This invention relates to a continuous flow system automatic analyzing method and apparatus. More particularly, the present invention relates to an automatic analyzing method and apparatus which consumes a reduced quantity of a reagent and has high reliability.

Continuous flow analysis comprises forming a continuous flow of a reagent or a carrier solution, charging a sample into the continuous flow and guiding the flow to a detector for measurement. This analysis has gained a wide application in automatic analyzers because it provides the advantages that the measuring time can be shortened, not only the reaction result but also the reaction process can be measured and only a trace amount of sample is necessary. An example of the continuous flow analyzer of the prior art is disclosed in U.S. Pat. No. 4,022,575, for example. In accordance with this prior art, a carrier stream is formed by a reagent and a necessary amount of sample is charged into the stream. Though this method has the large advantage that the construction is simple, it is not free from the disadvantage that the reagent must be constantly caused to flow and hence, a large amount of reagent is necessary. In addition, the liquid pressure and flow velocity in the flow path must be accurate and stable because the time from introduction of the sample till measurement and the time required for the sample to pass through the reaction portion significantly affect the measuring accuracy. Accordingly, a waiting time is necessary from the start of operation of a pump till the start of analysis so as to stabilize the flow and the reagent is consumed in vain in the interim. If the analyzing method is changed, large quantities of reagent must also be caused to flow in order to replace the reagents.

British Laid-Open Pat. No. 2,023,286 discloses an apparatus as an improvement over the conventional continuous flow analyzer of the kind described above. In this improved apparatus, two carrier flow paths are disposed and one is used as a sample introduction path with the other, as a reagent introduction path. Both flow paths are joined together on the downstream side into a single flow path and the reagent and the sample are guided to the reaction portion. Accordingly, the carrier liquid is always caused to flow through the path and the condition of the path is kept stable. The reagent in a necessary amount is introduced in synchronism with the introduction of the sample only at the time of analysis so that the reagent can be saved. In addition, the reagents can be easily replaced when the analyzing method is changed.

However, the drawback of this improved apparatus is that since two carrier flow paths are disposed, two liquid feed pumps must be disposed and the overall size of the apparatus becomes great. In this apparatus, the performance of the pumps affect significantly the accuracy of analysis so that high precision pumps must be employed, resulting eventually in the increase of the cost of production. Hence, the number of pumps is preferably as small as possible.

SUMMARY OF THE INVENTION

It is therefore an object of the present invention to provide a continuous flow system analyzer which has high accuracy of analysis and high reliability.

It is another object of the present invention to provide a continuous flow system analyzer which is simple in construction and yet has a stable carrier stream.

It is still another object of the present invention to provide a continuous flow system analyzer which can charge both reagent and sample into a carrier stream or into a reaction portion at a suitable timing.

It is a further object of the present invention to provide a continuous flow system analyzer which consumes only a reduced quantity of reagent.

The present invention is characterized in that a carrier liquid is caused to continuously flow into a single tubular conduit to form a continuous carrier stream and predetermined volumes of reagent and sample are charged into the carrier stream either in series or in the state in which the sample is interposed between the reagent.

These and other objects and features of the present invention will become more apparent from the following detailed description as well as from the appended claims.

DESCRIPTION OF THE PREFERRED EMBODIMENTS

Figure 1A:
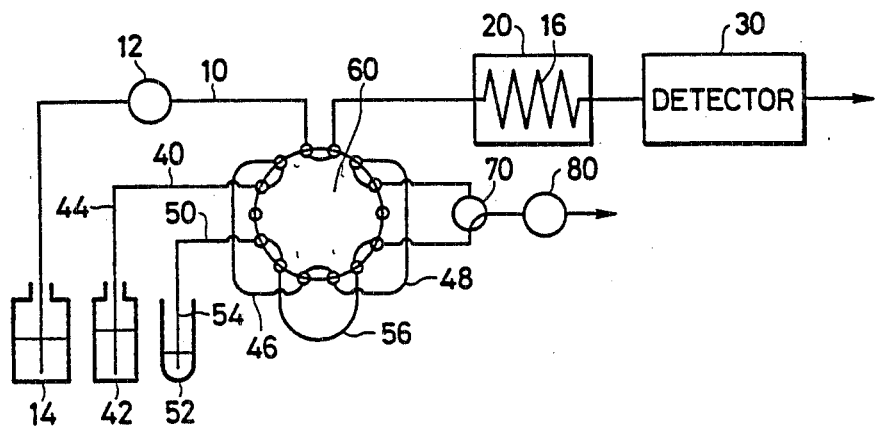
FIGS. 1A and 1B diagrammatically illustrate the construction of the continuous flow system analyzer in accordance with one embodiment of the present invention.

In one embodiment of the present invention shown in FIG. 1A, a reaction portion 20 and a detector 30 are connected to a main carrier conduit 10 through which the carrier liquid is caused to flow continuously. A reagent conduit 40 and a sample conduit 50 are connected to the main carrier conduit 10 via a rotary valve 60 and are selectively connected and disconnected to and from the main conduit by the operation of the rotary valve 60.

A peristaltic pump is used as the carrier liquid pump 12 and feeds at a constant flow velocity the carrier liquid (distilled water) from a carrier liquid container 14 to the reaction portion 20 and to the detector 30 through the main carrier conduit 10, forming a stable carrier stream. A reaction coil 16 is disposed in the reaction portion 20.

One end of the reagent conduit 40 is connected to a pump 80 via a first reagent metering pipe 46, a second reagent metering pipe 48 and change-over valve 70 that are connected to the rotary valve 60. A reagent probe 44 is connected to the other end of the reagent conduit 40 and sucks the reagent liquid from the reagent container 42. Similarly, one end of the sample conduit 50 is connected to the pump 80 via a sample metering pipe 56 and the change-over valve 70 that are connected to the rotary valve 60. A sample probe 54 is connected to the other end of the sample conduit 50 and sucks the sample from a sample container 52. In the state shown in the drawing, the change-over valve 70 connects the pump 80 to the sample flow system and introduces the sample from the sample container 52 into the sample metering pipe 56. Next, the change-over valve 70 is changed over to the reagent flow system and introduces the reagent liquid from the reagent container 42 into the reagent metering pipes 46, 48.

In the state shown in FIG. 1A, the main conduit 10 is cut off from the reagent flow system 40 and from the sample flow system by the rotary valve 60. Each of the reagent metering pipes 46, 48 and the sample metering pipe 56 has an inner diameter and length so that its volume coincides with the volumes of reagent and sample necessary for the analysis. According to this arrangement, the accurate and necessary volumes of reagent and sample for the analysis are introduced into the respective pipes upon the operation described above.

Figure 1B:
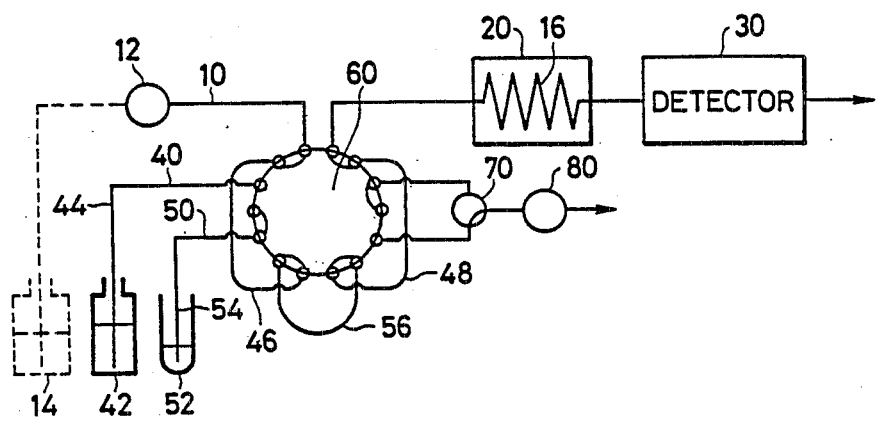

After the reagent and the samples are introduced into the respective pipes in the manner described above, the rotary valve 60 rotates and forms the flow path shown in FIG. 1B. In the drawing, one end of the reagent matering pipe 46 filled with the reagent liquid is connected to one end of the sample metering pipe 56 filled with the sample liquid and the other end of the sample metering pipe 56 is connected to one end of another reagent metering pipe 48. Accordingly, the sample liquid in the sample metering pipe 56 comes into contact in series with, and interposed by, the reagent in the two reagent metering pipes 46 and 48. The other end each of the reagent metering pipes 46, 48 is connected to the main conduit 10 filled with the carrier liquid. In other words, a flow path is defined in which the sample liquid, which is interposed between the reagent liquid, is introduced into the carrier stream. When the carrier pump 12 is operated under this state, the sample liquid is supplied to the reaction coil 16 while being interposed between the reagent liquid. During the period in which the sample liquid introduced into the main carrier stream passes through the reaction coil 16, it undergoes the reaction with the reagent and measurement is effected by the detector 30.

The embodiment described above employs the system in which two reagent metering pipes are disposed so as to introduce the sample into the main carrier stream while the sample is being interposed between the reagent liquid, but either of the reagent pipes may be deleted. In short, it is only necessary that the sample liquid be introduced into the main carrier stream while it keeps contact with the reagent liquid. If both reagent metering pipe and sample metering pipe are detachable, the metering pipes having different capacities can be fitted in accordance with the sample and reagent in the volumes necessary for the analysis, thus making it possible to make the continuous flow system more convenient.

In this embodiment, measurement can be carried out using the minimal necessary volumes of sample and reagent. The detection accuracy of the reaction condition can be also improved because the sample is introduced in series while being interposed between the reagent liquid and the stable flow path is constantly formed by the carrier stream.

Figure 2A:
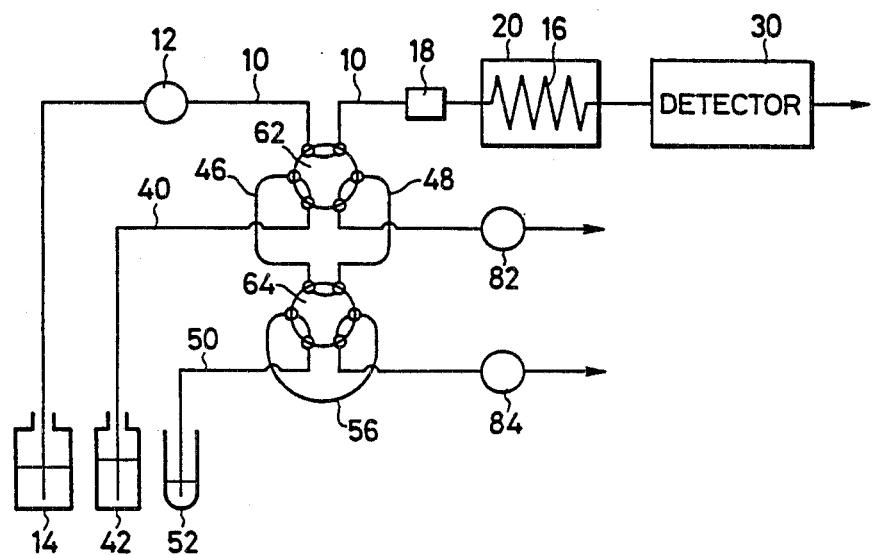
FIGS. 2A and 2B diagrammatically illustrate the construction of the continuous flow system analyzer in accordance with another embodiment of the present invention.

FIG. 2A shows another embodiment of the present invention, in which like reference numerals are used to identify like constituents as in FIG. 1A. The basic construction of this embodiment is the same as the foregoing embodiment shown in FIG. 1A. The main carrier stream is formed in the main carrier conduit 10. In this embodiment, the separate rotary valves and pumps are used for the reagent liquid and for the sample liquid, respectively. As shown in the drawing, the rotary valve 62 and pump 82 for the reagent are connected to the reagent conduit 40, and the rotary valve 64 and pump 84 for the sample are likewise connected to the sample conduit 50. The rotary valves 62 and 64 can be interconnected to each other while the rotary valve 62 can be interconnected to the main carrier conduit 10. Under the state shown in FIG. 2A, the stable carrier stream is formed as the main carrier conduit 10 is cut off from both reagent flow system and sample flow system.

On the other hand, the reagent rotary valve 62 is also cut off from the sample flow path so that the carrier stream, the reagent flow system and the sample flow system form the independent flow systems, respectively. The reagent liquid in the reagent container 42 enters the reagent pump 82 and is introduced into and metered by the reagent metering pipes 46, 48. The sample in the sample container 52 is introduced into and metered by the sample metering pipe 56.

Figure 2B:
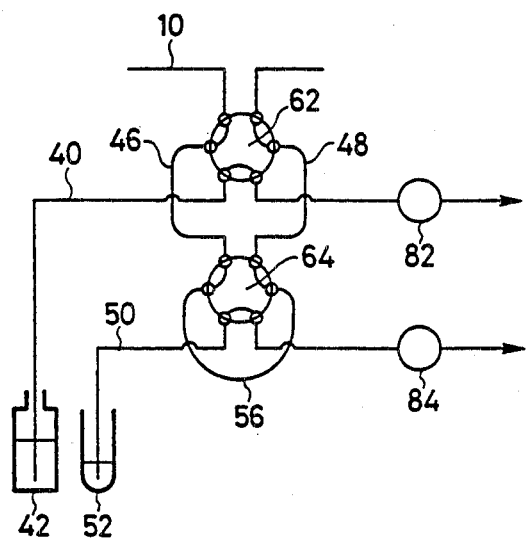

Thereafter, the rotary valves 62 and 64 are rotated to change the state of interconnection as shown in FIG. 2B. In the drawing, one end each of the reagent metering pipes 46, 48 of the reagent rotary valve 62 is connected to the sample metering pipe 56 of the rotary valve 64 so that the sample liquid is interposed in series between the reagent liquid. On the other hand, the other end each of the reagent metering pipes 46, 48 is inserted into and connected to the main carrier conduit 10. Accordingly, the sample that is interposed between the reagent liquid is introduced in series into the main carrier stream. In this embodiment, the mixer 18 is connected to the main carrier conduit and mixes the sample with the reagent. This embodiment provides the same effect as the foregoing embodiment shown in FIG. 1A. Additionally, this embodiment makes it possible to simplify the construction of each rotary valve and a common driving source can be used in common for both rotary valves because they can be changed over simultaneously. Though this embodiment uses two pumps, the performance of the pumps 82, 84 does not affect the accuracy of analysis because metering of the reagent and sample is effected by the respective metering pipes and introduction of the sample and reagent into the main carrier stream is carried out by the rotary valve and the carrier pump 12. Hence, economical pumps can be employed.

The rotary valve to be used in the embodiments shown in FIGS. 1A and 2A may have a known, commercially available construction. An example of the construction is shown in FIGS. 3 and 4.

Figure 3:
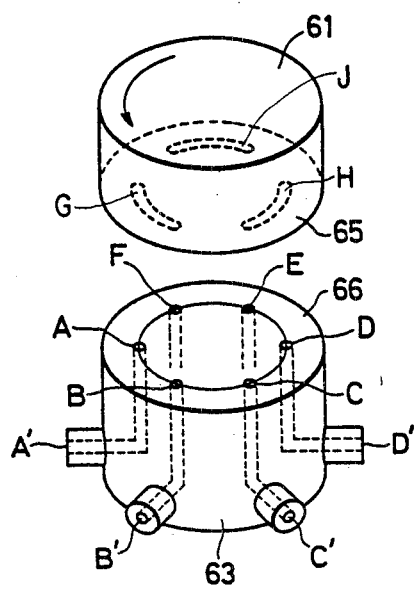
FIG. 3 diagrammatically illustrates the construction of a rotary valve used in the embodiments of the present invention.
Figure 4A:
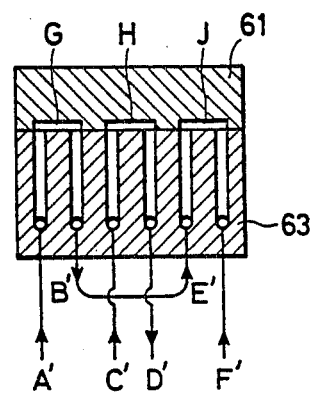
FIGS. 4A and 4B are partial sectional views useful for explaining the change-over operation of the rotary valve shown in FIG. 3.
Figure 4B:
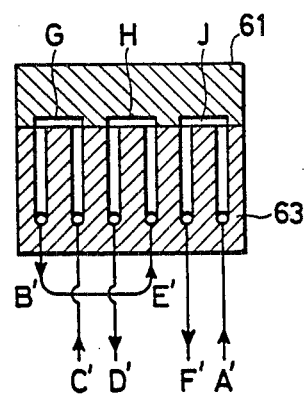

FIG. 3 is a schematic view showing the appearance of the rotary valve. The rotary valve 60 consists of a rotary portion 61 and a fixed portion 63 and is constructed so that slide surfaces 65 and 66 slide while keeping contact with each other under the air-tight state. Change-over holes A through F are bored on the slide surface 66 of the fixed portion 63 and communicate with passages A' through F', respectively. Groove holes G, H and J are defined on the slide surface 65 of the rotary portion 61. Connection of the passages is shown in FIGS. 4A and 4B. Referring to FIG. 4A, when the sample is introduced from the passage A' into F', the passages B' through F' serve as the sample metering pipes and the volume of the sample is determined by this length. The passages C', D' are for introducing the sample into the main carrier conduit, for example and the carrier liquid or the reagent liquid is caused to flow in this case. When the rotary portion 61 is rotated under this state and the state of connection is changed over as shown in FIG. 4B, the metered sample is connected to the passages C', D' and is introduced into the main carrier stream.

In both of the embodiments shown in FIGS. 1 and 2, after the sample and the reagent are introduced into the main carrier conduit, the change-over valve is changed over so as to cut them off from the main carrier conduit and the change-over valve can suck and meter the subsequent sample and reagent during the period in which analysis is carried out in the main carrier conduit. Accordingly, the next sample can be introduced immediately after completion of analysis of the previous sample. Moreover, even before the analysis of the previous sample is not yet completed, the sample can be introduced sequentially with such an interval in which the previous sample does not overlap with the next sample. The method of analysis can be easily changed over by replacing the reagent container by the reagent container for another analytical method.

As described in the foregoing, the present invention makes it possible to reduce consumption of the reagent and to improve the reliability.

What is claimed is:

1. An apparatus for flow analysis of a liquid sample, comprising: means for introducing a carrier liquid into a main single tubular conduit to form a carrier stream; a reagent metering pipe having a predetermined capacity; means for introducing a reagent liquid into the reagent metering pipe; a sample metering pipe having a predetermined capacity; means for introducing a sample liquid into the sample metering pipe; means for connecting the reagent metering pipe and the sample metering pipe with each other in series and for connecting the main conduit with the reagent metering pipe and the sample metering pipe so that the reagent liquid from the reagent metering pipe and the sample liquid from the sample metering pipe can be carried in series into the main conduit by directing the carrier liquid from said main conduit into the reagent metering pipe and the sample metering pipe; means for reacting said sample liquid with said reagent liquid; and means for detecting a reaction condition of said sample liquid with said reagent liquid.

2. An apparatus for flow analysis of a liquid sample, comprising: a main single tubular conduit; means for introducing a carrier liquid into the main single tubular conduit to form a carrier stream; first and second reagent metering pipes having a predetermined capacity, each of said first and second metering pipes having first and second ends; means for introducing a reagent liquid into the first and second reagent metering pipes; a sample metering pipe having a predetermined capacity; means for introducing a sample liquid into the sample metering pipe; means for connecting the sample metering pipe between the first ends of each of the first and second reagent metering pipes so that the first reagent metering pipe, the sample metering pipe and the second reagent metering pipe are in series, and for connecting the second end of each of the first and second reagent pipes with the main conduit; means for reacting said sample liquid with said reagent liquid; and means for detecting a reaction condition of said sample liquid with said reagent liquid.

3. An apparatus for flow analysis of a liquid sample comprising: a first pipe means for metering a liquid sample of a predetermined volume; means for introducing the liquid sample into the first pipe means; second pipe means for metering a reagent solution of a predetermined volume; means for introducing the reagent solution into the second pipe means; a reaction zone to react the sample with the reagent; a detection zone to detect the sample reacting with the reagent; a main conduit for forming a carrier stream of a carrier liquid; means for directing the carrier stream to the reaction zone and the detection zone; means for cutting off the first pipe means from the main conduit when the sample is introduced into the first pipe means and for cutting off the second pipe means from the main conduit when the reagent is introduced into the second pipe means; means for connecting the first and second pipe means in series; means for communicating the main conduit with the first and second pipe means connected in series for introducing the sample and the reagent into the main conduit in series by diverting the carrier stream so as to pass the carrier stream through the first and second pipe means connected in series.

4. An apparatus for flow analysis of a liquid sample, comprising: a sample metering pipe having first and second ends; a first reagent metering pipe having first and second ends; a second reagent metering pipe having first and second ends; a reaction zone to react a sample with a reagent; a detection zone to detect the sample reacted with the reagent; a main conduit for carrying a carrier stream of a carrier liquid; means for directing the carrier stream to the reaction zone and the detection zone; and means for connecting the first end of the sample metering pipe with the first end of the first reagent metering pipe, for connecting the second end of the sample metering pipe with the first end of the second reagent metering pipe, and for connecting the second ends of each of the first and second reagent metering pipes with the main conduit, so that the carrier stream may be passed through the first reagent metering pipe, the sample metering pipe and the second reagent metering pipe.

5. An apparatus for flow analysis of a liquid sample, comprising: detecting means for detecting a reaction condition of a sample liquid with a reagent liquid; a main conduit for forming a carrier stream of a carrier liquid; means for directing the carrier liquid in the main conduit toward the detecting means; a single metering pipe, having first and second ends, for the introduction of a sample liquid therein; two reagent metering pipes, each having first and second ends, for the introduction of the reagent liquid therein; valve means for connecting the first end of the sample metering pipe to the first end of one of the reagent metering pipes, for connecting the second end of the sample metering pipe to the first end of the other reagent metering pipe, for connecting the second ends of each of the two reagent metering pipes to the main conduit, for cutting off the sample metering pipe from the main conduit and for cutting off the two reagent metering pipes from the main conduit; means for introducing the sample liquid into the sample metering pipe when the valve means cuts off the sample metering pipe from the main conduit; and means for introducing the reagent solution into the two reagent metering pipes when the valve means cuts off the two reagent metering pipes from the main conduit.

6. An apparatus according to claim 5, wherein said valve means comprises a rotary valve.

7. An apparatus for flow analysis of a liquid sample, comprising: means for detecting a reaction condition of a sample liquid with a reagent liquid; a main conduit for forming a carrier stream of a carrier liquid; means for directing the carrier liquid in the main conduit toward the detecting means; a single sample metering pipe, having first and second ends, for the introduction of the sample liquid therein; two reagent metering pipes, each having first and second ends, for the introduction of the reagent liquid therein; a first connecting means selectively connected to the main conduit and a second connecting means selectively connected to the sample metering pipe; wherein the first end of each of the two reagent metering pipes is connected to the first connecting means, the second end of each of the two reagent metering pipes is connected to the second connecting means and the first and second ends of the sample metering pipe are connected to the second connecting means; the first and second connecting means each having two operative positions, one of the operative positions allowing the main conduit, the two reagent metering pipes and the sample metering pipe to be independent of one another and the second operative position allowing the main conduit, the two reagent metering pipes and the sample metering pipe to be connected in series.

8. An apparatus according to claim 7, wherein said first and second connecting means comprise rotary valve means.

* * * * *